(12) United States Patent
Scheel-Krüger et al.

(10) Patent No.: US 6,395,748 B2
(45) Date of Patent: *May 28, 2002

(54) TROPANE-DERIVATIVES, THEIR PREPARATION AND USE

(75) Inventors: Jørgen Scheel-Krüger, Glostrup; Peter Moldt, Humlebaek; Frank Wätjen, Herlev, all of (DK)

(73) Assignee: NeuroSearch A/S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/814,413

(22) Filed: Mar. 21, 2001

Related U.S. Application Data

(63) Continuation of application No. 09/101,524, filed as application No. PCT/EP97/00850 on Feb. 21, 1997, now Pat. No. 6,288,079.

(30) Foreign Application Priority Data

Feb. 22, 1996 (DK) .............................. 0194/96

(51) Int. Cl.$^7$ .......................... A61K 31/46; A61P 25/28
(52) U.S. Cl. ..................................... 514/304
(58) Field of Search ........................ 514/304

(56) References Cited

U.S. PATENT DOCUMENTS

| | | | | |
|---|---|---|---|---|
| 4,281,130 A | * | 7/1981 | Clarke | 546/63 |
| 5,380,848 A | * | 1/1995 | Kuhar et al. | 546/124 |
| 5,413,779 A | * | 5/1995 | Kuhar et al. | 424/1.85 |
| 5,496,953 A | * | 3/1996 | Kuhar et al. | 546/125 |

FOREIGN PATENT DOCUMENTS

| | | | |
|---|---|---|---|
| EP | 0 604 352 A | * | 6/1994 |
| EP | 0 604 354 A | * | 6/1994 |
| EP | 0 604 355 A | * | 6/1994 |
| WO | 93 09814 A | * | 5/1993 |
| WO | 95 28401 A | * | 10/1995 |

OTHER PUBLICATIONS

Sramek JJ and Cutler NR. Alzheimer Disease and Associated Disorders. (Oct.–Dec., 2000), 14(4) 216–27.*
Brinton DR and Yamzaki RS. Pharmaceutical Research. (Mar. 1998), 15(3) 386–98.*
Bennett, B.A., et al., "Novel 2–substituted cocaine analogs: uptake and ligand binding studies at dopamine, serontonin and norepinephrine transport sites in the rat brain", *J. Pharmacol. Exp. Ther.*, vol. 272, No. 3, 1176–1186, (1995).*
Clarke, R.L., et al., "Compounds Affecting the Central Nervous System.4. 3B–Phenyltropane–2–carboxylic Esters and Analogs", *Journal of Medicinal Chemistry*, vol. 16, No. 11, p. 1260–1267, (1973).*
Kelkar, S.V., et al., "Synthesis, cocaine receptor affinity, and dopamine uptake inhibition of several new 2–beta–substituted 3–beta–phenyltropanes", *J. Med. Chem.*, vol. 37, No. 23, 3875–3877, (1994).*
Kozikowski, et al., "Chemistry and biology of the 2–beta–alkyl–3–beta–phenyl analogous of ococaine", *J. Med. Chem*, vol. 38, No. 16, 3086–3093, (1995).*

* cited by examiner

*Primary Examiner*—Evelyn Mei Huang
(74) *Attorney, Agent, or Firm*—Schwegman, Lundberg, Woessner & Kluth, P.A.

(57) ABSTRACT

Compounds of formula (a), (b), (c), or (d), or any mixture thereof, or a pharmaceutically-acceptable salt thereof;

(a)

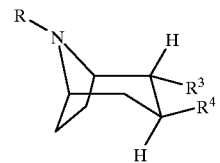

(b)

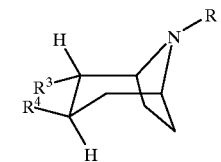

(c)

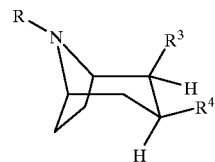

(d)

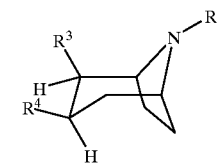

wherein R is hydrogen, alkyl, alkenyl, alkynyl, cycloalkyl, cycloalkylalkyl or 2-hydroxyethyl; $R^3$ is —CH$_2$—X—R', wherein X is O, S or NR", wherein R" is hydrogen or alkyl and R' is alkyl, alkenyl, alkynyl, cycloalkyl, cycloalkylalkyl, or —CO-alkyl; $R^4$ is phenyl optionally substituted with halogen, CF$_3$, CN, alkoxy, cycloalkoxy, alkyl, cycloalkyl, alkenyl, alkynyl, amino, nitro, heteroaryl, or aryl; 3,4-methylenedioxyphenyl; benzyl optionally substituted with halogen, CF$_3$, CH, alkoxy, cycloalkoxy, alkyl, cycloalkyl, alkenyl, alkynyl, amino, nitro, heteroaryl, or aryl; heteroaryl optionally substituted with halogen, CF$_3$, CN, alkoxy, cycloalkoxy, alkyl, cycloalkyl, alkenyl, alkynyl, amino, nitro, heteroaryl, or aryl; or naphthyl optionally substituted with halogen, CF$_3$, CN, alkoxy, cycloalkoxy, alkyl, cycloalkyl, alkenyl, alkynyl, amino, nitro, heteroaryl, or aryl. The compounds are monoamine neurotransmitter, i.e., dopamine, serotonin, noradrenaline, reuptake inhibitors.

7 Claims, No Drawings

TROPANE-DERIVATIVES, THEIR PREPARATION AND USE

The present application is a continuation of U.S. application Ser. No. 09/101,524, filed Jul. 10, 1998, now U.S. Pat. No. 6,288,079, which is a U.S. National Application filed under 35 USC 371 of PCT/EP97/00850, filed Feb. 21, 1997 based on Danish application Serial No. DK 0194/96, filed Feb. 22, 1996.

The present invention relates to novel tropane-derivatives which are valuable monoamine neurotransmitter, i.e dopamine, serotonin and noradrenaline, re-uptake inhibitors and the use of the novel tropane derivatives for the treatment of disorders or diseases responsive to the inhibition of monoamine neurotransmitter re-uptake, such as Parkinson's disease, depression, obsessive compulsive disorders, panic disorders, dementia, memory deficits, attention deficit hyperactivity disorder, obesity, anxiety, eating disorders and drug addiction or misuse, including cocaine abuse.

BACKGROUND OF THE INVENTION

The brain consists of a plurality of neurons that communicate with each other via chemical messengers. Each neuron generates neurochemicals or neurotransmitters which act at sites being referred to as receptors on the cellular membrane of neurons. One group of neurotransmitters, referred to as the monoamine neurotransmitters, includes serotonin, dopamine and noradrenaline.

Monoamine neurotransmitters are released into the synaptic cleft between neurons in order to stimulate postsynaptic receptor activity. The removal (or inactivation) of monoamine neurotransmitters occurs mainly by a reuptake mechanism into the presynaptic terminals. By inhibiting the re-uptake an enhancement of the physiological activity of monoamine neurotransmitters occur.

The serotonergic neural system of the brain have been shown to influence a variety of physiologic functions, and compounds having serotonin re-uptake inhibiting activity are predicted to have the ability to treat in mammals, including humans, a variety of disorders associated with this neural system, for example eating disorders, depression, obsessive compulsive disorders, panic disorders, alcoholism, pain, memory deficits and anxiety. Included among these disorders are disorders related to depression, such as pseudodementia or Ganser's syndrome, migraine pain, bulimia, obesity, pre-menstrual syndrome or late luteal phase syndrome, tobacco abuse, panic disorder, post-traumatic syndrome, memory loss, dementia of ageing, acquired immunodeficency syndrome dementia complex, memory dysfunction in ageing, social phobia, attention deficit hyperactivity disorder, chronic fatigue syndrome, premature ejaculation, erectile difficulty, anorexia nervosa, disorders of sleep, autism, mutism or trichotillomania.

The pathophysiology of major affective illness is poorly understood, and several neurotransmitters have been implicated in the pathophysiology of major depression.

Mixed noradrenalin and serotonin re-uptake inhibitors, such as Imipramine and Amitriptyline and noradrenaline-reuptake inhibitors, such as Desipramine, Nortriptyline, and Protriptyline are currently used pharmaceuticals in anti-depressant therapy. Moreover, several lines of preclinical and clinical evidence indicate that an enhancement of serotonin-mediated neurotransmission might underlie the therapeutic effect of the most recent and currently used drugs in anti-depressant therapy: Fluoxetine, Citalopram and Paroxetine.

Paradoxical currently used serotonin re-uptake inhibitors inhibit the serotonin transporter within minutes whereas their full anti-depressant effect is seen only after three to four weeks of treatment, indicating that re-uptake inhibition per se is not responsible for the antidepressant response, but rather that further adaptive changes underlie and/or contribute to their therapeutic effect. The delayed onset of anti-depressant effect is considered to be a serious drawback to currently used monoamine re-uptake inhibitors.

A strong dopamine re-uptake inhibiting activity is considered with the risk of undesirable central stimulating effects. On the other hand, an activating effect on the mesolimbic dopamine system is believed to underlay the commen mechanism of current antidepressant treatment by a mechanism which enhances the endogenous reward system. Compounds with a strong serotonin re-uptake inhibiting activity combined with a well balanced moderate dopamine re-uptake inhibiting activity may therefore provide agents with a rapid onset of anti-depressant effect.

The compounds of the present invention are also valuable dopamine reuptake inhibitors and are as such considered useful for the treatment of Parkinsonism, depression, obesity, narcolepsy, drug addiction or misuse, including cocaine abuse, attention-deficit hyperactivity disorders, Gilles de la Tourettes disease and senile dementia. Dopamine re-uptake inhibitors enhances indirectly via the dopamine neurones the release of acetylcholin and are therefore also useful for the treatment of memory deficits, e.g. in Alzheimers disease, presenile dementia, memory dysfuntion in ageing, and chronic fatigue syndrome. Noradrenaline re-uptake inhibitors are considered useful for enhancing attention, alertness, arousal, vigilance and for treating depression.

OBJECTS OF THE INVENTION

It is an object of the present invention to provide novel tropane-derivatives which are monoamine neurotransmitter re-uptake inhibitors and therefore useful for the treatment of disorders such as Parkinson's disease, depression and related diseases, obsessive compulsive disorders, panic disorders, dementia, memory deficits, attention deficit hyperactivity disorder, obesity, anxiety, eating disorders, drug addiction or misuse, including cocaine abuse.

Another object of the present invention is to provide novel pharmaceutical compositions containing the novel tropane-derivatives.

Still another object of the invention is to provide a method of treating diseases or disorders responsive to the inhibition of monoamine neurotransmitter re-uptake, such as Parkinsonism, depression and related diseases, obsessive compulsive disorders, panic disorders, dementia, memory deficits, attention deficit hyperactivity disorder, obesity, anxiety, eating disorders, drug addiction or misuse, including cocaine abuse.

Other objects will become apparent hereinafter to one skilled in the art.

The Present Invention

The invention then, inter alia, comprises the following, alone or in combination:

A compound having the formula,

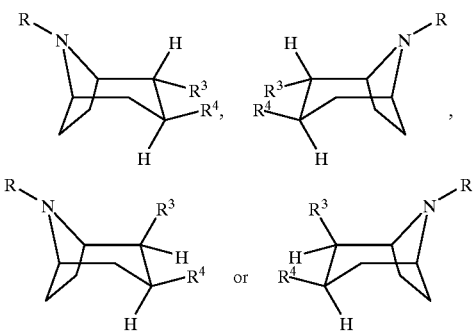

or any mixture thereof, or a pharmaceutically acceptable salt thereof;
wherein
R is hydrogen, alkyl, alkenyl, alkynyl, cycloalkyl, cycloalkylalkyl or 2-hydroxyethyl;
$R^3$ is $CH_2$—X—R', wherein X is O, S, or NR", wherein R" is hydrogen, or alkyl, and R' is alkyl, alkenyl, alkynyl, cycloalkyl, cycloalkylalkyl, or —CO-alkyl;
$R^4$ is
  phenyl which may be substituted one or more times with substituents selected from the group consisting of halogen, $CF_3$, CN, alkoxy, cycloalkoxy, alkyl, cydoalkyl, alkenyl, alkynyl, amino, nitro, heteroaryl and aryl;
  3,4-mothylenedioxyphenyl;
  benzyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
  heteroaryl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl; or
  naphthyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
a compound as above which is
2-methoxymethyl-3-(3,4-dichlorophenyl)-tropane,
2-isopropoxymethyl-3-(3,4-dichlorophenyl)-tropane,
2-ethoxymethyl-3-(3,4-dichlorophenyl)-tropane,
2-cyclopropylmethyloxymethyl-3-(3,4-dichlorophenyl)-tropane,
2-methoxymethyl-3-(4-chlorophenyl)-tropane,
N-Normethyl-2-methoxymethyl-3-(4-chlorophonyl)-tropane,
2-ethoxymethyl-3-(4-chlorophenyl)-tropane,
N-normethyl-2-methoxymethyl-3-(3,4-dichlorophenyt)-tropane,
N-normethyl-2-ethoxymethyl-3-(3,4-dichlorophenyl)-tropane,
N-Normethyl-2-ethoxymethyl-3-(4-chlorophonyl)-tropane,
2-ethylthiomethyl-3-(3,4-dichlorophenyl)-tropane,
2-cyclopropylmethyloxymethyl-3-(4-chlorophenyl)-tropane, or
N-normethyl-2-cyclopropylmethyloxymethyl-3-(4-chlorophenyl)-tropane,
or a pharmaceutically acceptable addition salt thereof;
a compound as above which is
(1R, 2R, 3S)-2-methoxymethyl-3-(3,4-dichlorophenyl)-tropane,
(1R, 2R, 3S)-2-isopropoxymethyl-3-(3,4dichlomphenyl)-tropane,
(1R, 2R, 3S)-2-ethoxymethyl-3-(3,4dichlorophenyl)-tropane,
(1R, 2R, 3S)-2-cyclopropylmethyloxymethyl-3-(3,4-dichlorophenyl)-tropane,
(1R, 2R, 3S)-2-methoxymethyl-3-(4chlorophenyl)-tropane,
(1R, 2R, 3S)-N-Normethyl-2-methoxymethyl-3-(4-chlorophenyl)-tropane,
(1R, 2R, 3S)-2-ethoxymethyl-3-(4-chlorophenyl)-tropane,
(1R, 2R, 3S)-normethyl-2-methoxymethyl-3-(3, 4dichlorophenyl)-tropane, (1R, 2R, 3S)-N-normethyl-2-ethoxymethyl-3-(3,4-dichlorophenyl)-tropane,
(1R, 2R, 3S)-N-Normethyl-2-ethoxymethyl-3-(4-chlorophenyl)-tropane,
(1R, 2R, 3S)-N-normethyl-2cyclopropylmethyloxymethyl-3-(4-chlorophenyl)-tropane,
(1R, 2R, 3S)-2-cyclopropylmethyloxymethyl-3-(4chlorophenyl)-tropane, or (1R, 2R, 3S)-2-ethylthiomethyl-3-(3,4dichlorophenyl)-tropane,
or a pharmaceutically acceptable addition salt thereof;
a pharmaceutical composition, comprising an therapeutically effective amount of a compound as any above, or a pharmaceutically acceptable addition salt thereof, together with at least one pharmaceutically acceptable carrier or diluent;
the use of a compound as any above for the manufacture of a medicament for the treatment of a disorder or disease of a living animal body, including a human, which disorder or disease is responsive to the inhibition of monoamine neurotransmitter reuptake in the central nervous system;
the use of a compound as above for the manufacture of a medicament for the treatment of parkinsonism, depression, pseudodementia, obesity, narcolepsy, drug addiction and/or abuse, attention-deficit hyperactivity disorders, senile dementia, or cognitive dysfunction;
a method for the preparation of the compounds as above comprising the step of reacting a compound having the formula

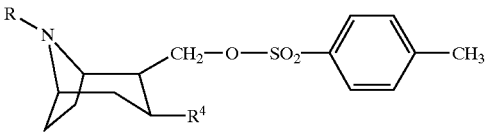

or any of its enantiomers or any mixture thereof, wherein R and $R^4$ is as defined in claim 1, with an alcoholate R'—Z—Na, wherein R' is as defined in claim 1 and Z is O, or S to form a compound of the invention wherein X is O, or S;
reacting a compound having the formula

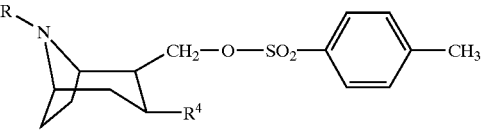

or any of its enantiomers or any mixture thereof, wherein R and $R^4$ is as defined in claim 1, with an amine NHR"—R' to form a compound of the invention wherein X is NR"; or reacting a compound having the formula

[Structure: bicyclic compound with R-N, CH₂-O-H, and R⁴ substituents]

or any of its enantiomers or any mixture thereof, wherein R and $R^4$ is as defined in claim 1, with sodium hydride and a compound having the formula R'—SO$_2$ to form a compound of the invention wherein X is O;

a method of treating a disorder or disease of a living animal body, including a human, which disorder or disease is responsive to the inhibition of monoamine neurotransmitter reuptake, comprising the step of administering to such a living animal body, including a human, in need thereof a therapeutically effective amount of a compound as any above; and the method as above wherein parkinsonism, depression, pseudodementia, obesity, narcolepsy, drug addiction and/or abuse, attention-deficit hyperactivity disorders cognitive dysfunction, or senile dementia is treated.

Examples of pharmaceutically acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining compounds of the invention and their pharmaceutically acceptable acid addition salts.

Halogen is fluorine, chlorine, bromine or iodine.

Alkyl means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Cycloalkyl means cyclic alkyl of three to seven carbon atoms, including but not limited to cyclopropyl, cyclobutyl, cyclopentyl, and cyclohexyl;

Alkenyl means a group of from two to six carbon atoms, including at least one double bond, for example, but not limited to ethenyl, 1,2- or 2,3-propenyl, 1,2-, 2,3-, or 3,4-butenyl.

Alkynyl means a group of from two to six carbon atoms, including at least one triple bond, for example, but not limited to ethynyl, 2,3-propynyl, 2,3- or 3,4-butynyl.

Cycloalkylalkyl means cycloalkyl as above and alkyl as above, meaning for example, cyclopropylmethyl.

Alkoxy is O-alkyl, wherein alkyl is as defined above.

Cycloalkoxy is O-cycloalkyl, wherein cycloalkyl is as defined above.

Amino is NH$_2$ or NH-alkyl or N-(alkyl)$_2$, wherein alkyl is as defined above.

Heteroaryl is a 5 or 6-membered heterocyclic monocyclic group. Such an heteroaryl group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazolyl-4-yl, isothiazol-5-yl, 1,2, 4-oxadiazol-3-yl, 1,2, 4oxadiazol-5-yl, 1, 2, 4-thiadiazol-3-yl, 1, 2, 4-thiadiazol-5-yl, 1, 2, 5oxadiazol-3yl, 1, 2, 5-oxadiazol-4yl, 1, 2, 5thiadiazol-3-yl, 1, 2, 5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl and 3-pyrazinyl and 1-pyrazolyl, 3-pyrazolyl, and 4-pyrazolyl.

Aryl is an aromatic hydrocarbon, such as phenyl and naphthyl.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

It will be appreciated by those skilled in the art that the compounds of the present invention contain several chiral centres and that such compounds exist in the form of isomers (i.e. enantiomers). The invention includes all such isomers and any mixtures thereof including racemic mixtures.

Racemic forms can be resolved into the optical antipodes by known methods, for example, by separation of diastereomenic salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallizaton of d or l- (tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolvation of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

The following scheme illustrates methods by which the compounds of the invention can be prepared:

[Scheme: Starting material with CH₂OH group reacts with Tosyl Chloride to form tosylate (CH₂-O-SO₂-C₆H₄-CH₃), which then reacts with R'—Z—Na]

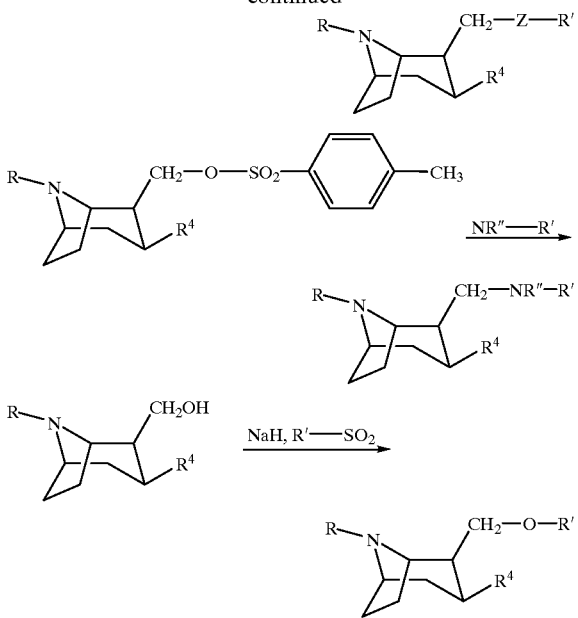

The processes in the reaction scheme above are carried out in conventional manner. The substituent Z in the above reaction scheme means O, or S.

Starting materials for the processes described in the present patent application are known or can be prepared by known processes from commercially available materials (see WO-95/28401).

A compound of the invention can be converted to another compound of the invention using conventional methods.

The products of the reactions described herein are isolated by conventional means such as extraction, crystallization, distillation, chromatography, and the like.

Biology

The compounds of the present invention have been tested for their ability to bind to the dopamine transporter in the following tests for in vitro inhibition of $^3$H-WIN 35428.

In vitro inhibition of $^3$H-WIN 35428 binding

Background:

Dopamine transporters/uptake sites on nerve terminals presumably function to terminate neuronal signaling by removing dopamine from the synaptic cleft. The activity or presence of the dopamine transporter integral protein can be measured in vitro with synaptosomal uptake of $^3$H-dopamine or membrane binding assays with $^3$H-ligands known to bind to the transporter.

In vitro binding studies of cocaine have demonstrated that cocaine binds to the dopamine transporter and inhibits $^3$H-dopamine uptake. Numerous ligands of several structural types have been reported to bind at the dopamine uptake site, but it remains questionable whether their binding sites are identical to that of cocaine. A structural analog of cocaine, $^3$H-WIN 35428, binds selectively and with high affinity to the dopamine transporter complex.

Tissue Preparation: Preparations are performed at 0–4° C. unless otherwise indicated. Corpus striatum from male Wistar rats (150–200 g) is homogenized for 5–10 sec in 10 ml NaH$_2$PO$_4$ (50 mM, pH 7.4) using an Ultra-Turrax homogenizer. The suspension is centrifuged at 27,000×g for 15 min. The supernatant is discarded and the pellet is resuspended in 50 mM NaH$_2$PO$_4$, pH 7.4 (1000 ml per g of original tissue) and used for binding assays.

Assay: Aliquots of 0.5 ml tissue are added to 25 ml of test solution and 25 ml of $^3$H-WIN 35428 (1 nM, final concentration), mixed and incubated for 60 min at 2° C. Non-specific binding is determined using cocaine (30 mM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

25–75% inhibition of specific binding must be obtained, before calculation of an IC$_{50}$. The test value is given as IC$_{50}$ (the concentration ($\mu$M) of the test substance which inhibits the specific binding of $^3$H-WIN 35428 by 50%).

The results obtained by testing compounds of the invention are given in the following table 1:

TABLE 1

| Test Compound | in vitro IC$_{50}$ $\mu$M |
|---|---|
| (1R,2R,3S)-2-methoxymethyl-3-(3,4-dichlorophenyl)-tropane, | 0.015 |
| (1R,2R,3S)-2-ethoxymethyl-3-(3,4-dichlorophenyl)-tropane, | 0.035 |

The test results presented above show that the compounds of the invention binds with high affinity to the dopamine transporter complex.

The compounds of the invention have also been tested for their ability to inhibit reuptake of dopamine(DA) noradrenaline(NA) and serotonin(5-HT) in synaptosomes.

Background:

Specific neurotransmitter transporters/uptake sites on nerve terminals presumably function to terminate neuronal signaling by removing the neurotransmitters dopamine, noradrenaline and serotonin, respectively, from the synaptic cleft. The activity of the transporter integral proteins can be measured in vitro by synaptosomal uptake of $^3$H-dopamine, $^3$H-noradrenaline and $^3$H-serotonin, respectively.

In vitro inhibition of $^3$H-dopamine (3H-DA) uptake in striatal synaptosomes

Tissue preparations: Preparations are performed at 0–40° C. unless otherwise indicated. Corpi striati from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet (P$_2$) is resuspended in oxygenated (equilibrated with an atmosphere of 96% O$_2$: 4% CO$_2$ for at least 30 min) Krebs-Ringer incubation buffer (8000 ml per g of original tissue) at pH 7.2 containing 122 mM NaCl, 0.16 mM EDTA, 4.8 mM KCl, 12.7 mM Na$_2$HPO$_4$, 3.0 mM NaH$_2$PO$_4$, 1.2 mM MgSO$_4$, 1 mM CaCl$_2$, 10 mM glucose and 1 mM ascorbic acid.

Assay: Aliquots of 4.0 ml issue suspension are added to 100 $\mu$l of test solution and 100 $\mu$l of $^3$H-DA (1 nM, final concentration), mixed and incubated for 25 min at 37° C. Non-specific uptake is determined using benztropine (10

μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-DA by 50%).

In vitro Inhibition of 3H-noradrenaline ($^3$H-NA) uptake in hippocampal synaptosomes Tissue preparation: Preparations are performed at 0–4° C. unless otherwise indicated. Hippocampi from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (2000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 0.97 mM $CaCl_2$, 10 mM glucose and 1 mM ascorbic acid.

Assay: Aliquots of 4.0 ml tissue suspension are added to 100 μl of test solution and 100 μl of $^3$H-NA (1 nM, final concentration), mixed and incubated for 90 min at 37° C. Non-specific uptake is determined using desipramine (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-NA by 50%).

In vitro inhibition of $^3$H-5-hydroxytryptamine ($^3$H-5-HT, serotonin) uptake in cortical synaptosomes Tissue preparation: Preparations are performed at 0–4° C. unless otherwise indicated. Cerebral cortices from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (1000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 1 mM $CaCl_2$, 10 mM glucose and 1 mM ascorbic acid.

Assay: Aliquots of 4.0 ml tissue suspension are added to 100 μl of test solution and 100 μl of $^3$H-5-HT (1 nM, final concentration), mixed and incubated for 30 min at 37° C. Non-specific uptake is determined using citalopram (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $Ic_{50}$ (the concentration (μM) of the test substance which inhibits the specific binding of $^3$H-5-HT by 50%).

Test results obtained by testing compounds of the present invention appear from the below table:

TABLE 2

| Test compound | DA-uptake $IC_{50}$ (nM) | NA-uptake $IC_{50}$ (nM) | 5-HT-uptake $IC_{50}$ (nM) |
|---|---|---|---|
| (1R,2R,3S)-2-methoxymethyl-3-(3,4-dichlorophenyl)-tropane, | 10 | 2 | 10 |
| (1R,2R,3S)-2-ethoxymethyl-3-(3,4-dichlorophenyl)-tropane, | 8 | 3.2 | 11 |
| (1R,2R,3S)-2-phenylthiomethyl-3-(3,4-dichlorophenyl)-tropane, | 4.3 | 2.8 | 9.2 |

The results presented above show that the compounds tested efficiently inhibits reuptake of dopamine, noradrenaline and serotonin in synaptosomes.

Pharmaceutical Compositions

While it is possible that, for use in therapy, a compound of the invention may be administered as the raw chemical, it is preferable to present the active ingredient as a pharmaceutical formulation.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are Included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such-as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of the present invention are useful in the treatment of disorders or diseases responsive to the monoamine neurotransmitter re-uptake inhibiting activity of the compounds. This activity of the compounds of the invention make them extremely useful in the treatment of, parkinsonism, depression, obesity, narcolepsy, drug abuse, e.g cocaine misuse, attention-deficit hyperactivity disorders, senile dementia and cognitive dysfunction as well as other disorders sensitive to the monoamine neurotransmitter reuptake-inhibiting activity of the compounds. The compounds of this invention may accordingly be administered to a living animal body, including a human, in need of treatment, alleviation, or elimination of an indication associated with or responsive to monoamine neurotransmitter uptake-inhibiting activity. This includes especially parkinsonism, depression, obesity, narcolepsy, cocaine abuse, attention-deficit hyperactivity disorders, senile dementia and memory dysfunction in ageing. Suitable dosage range are 0.1–500 milligrams daily, and especially 10–70 milligrams daily, administered once or twice a day, dependent as usual upon the exact mode of administration, form in which administered, the indication toward which the administration is directed, the subject involved and the body weight of the subject involved, and further the preference and experience of the physician or veterinarian in charge.

I.p. means intraperetoneally, which is a well known route of administration. P.o. means peroral, which is a well known route of administration.

The following examples will illustrate the invention further, however, they are not to be construed as limiting.

EXAMPLE 1

(−)-Anhydroecgonine methyl ester.

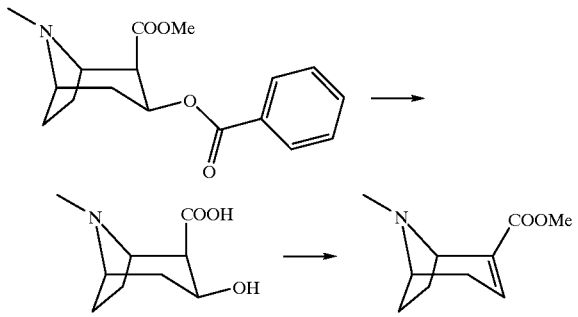

(1R, 2R, 3S)-2-Carbomethoxy-3-benzoxytropane, hydrochloride (100 g, 0.29 mol) was refluxed in 1000 ml 1M hydrochloric acid for 18 hours and the solution was ice cooled. Benzoic acid was collected by filtration and the filtrate was concentrated in vacuo. Trituration of the residue with ethanol and filtration yielded (1R, 2R, 3S)-3hydroxy-tropane-2-carboxylate, hydrochloride as a white crystalline compound which without further purification was dried and refluxed in phosphorous oxychloride (50 ml) for two hours. The solution was concentrated in vacuo and absolute methanol (150 ml) was slowly added under ice cooling. The solution was stirred at ambient temperature for 16 hours and was concentrated in vacuo. The residue was ice cooled and made basic by addition of a sodium hydroxide solution (10M, approximately 100 ml) and was extracted 5 times with diethyl ether. The combined organic phase was dried and concentrated in vacuo yielding oil, which was distilled in vacuo (70–74° C., 1 mBar) yielding the title compound as clear oil.

Alternatively (−)-Anhydroecgonine methyl ester was prepared as follows:

103 g (3.05 eqv.) sodium in 3.25 l abs ethanol was added 3 l ethylacetate (HPLC grade) and 500 g of cocaine hydrochloride. The reaction mixture was refluxed for 2.5 hours. 150 ml of acetic acid was added, pH~8, followed by 1.5 l of toluene. 2 l of solvents was evaporated under reduced pressure. Another 2 l of toluene was added, and another 2 l of solvents evaporated. This treatment was repeated once more. The total addition of toluene was 5.5 l and about 6 l of solvents was evaporated. The reaction mixture was filtered and the salts was washed with total 1 l of toluene. The solvent was evaporation under reduced pressure and the residue, 570 g, was distilled using a 15 cm Vigreux-column. Ethylbenzoate was distilled at 12 mmHg, b.p. 80–95° C. and the title compound was distilled without the Vigreux-column at 0.2–0.4 mbar, b.p. 56–80° C. The product was a clear, yellow liquid.

Yield: 218 g (76%).

EXAMPLE 2

(1R,2S,3S)-2-Carbomethoxy-3-(4-fluorophenyl)tropane and (1R, 2R, 3S)-2-carbomethoxy-3-(4-fluorophenyl)tropane

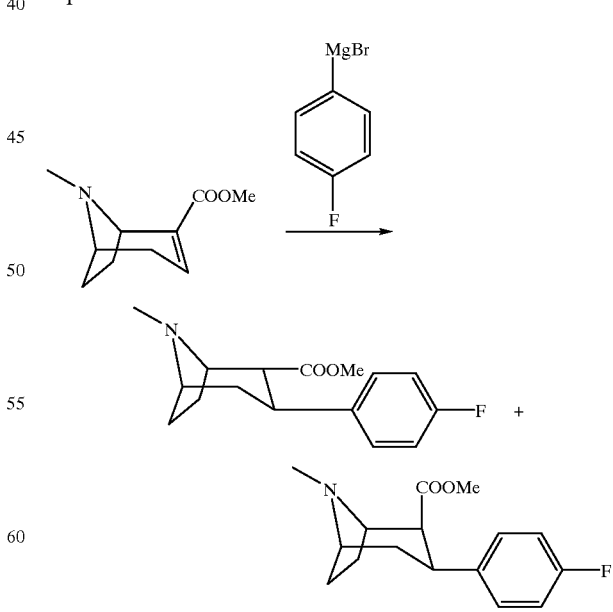

Grignard reagent was made in a three necked reaction flask equipped with mechanical stirring, an intensive condenser and a pressure equilibrated funnel, using 4bromofluorobenzene (27.5 ml, 250 mmol) and magnesium turnings (6.3 g, 260 mmol) in 250 ml absolute diethyl ether. The solution of grignard reagent was cooled to −20° C. and a solution of (−)-anhydroecgonine methyl ester (21.7 g, 120 mmol) in 100 ml absolute diethyl ether was added over ½ hour. The reaction was stirred one hour at −20° C. and the reaction was quenched in one of the following two ways:

1) The reaction mixture was stirred into 250 ml crushed ice and the water phase was made acidic by addition of approximately 100 ml 4M hydrochloric acid. The organic phase was discharged and the water phase was washed with 100 ml diethyl ether. The water phase was made basic by addition of 25% ammonium hydroxide solution, and was then saturated with sodium chloride and was finally extracted three times with diethyl ether. The combined organic phase was dried and concentrated in vacuo yielding oil which was distilled in vacuo (150–160° C., 2 mBar). This method yielded a mixture of two stereoisomers (2S/2R - ⅓) which was separated by column chromatography using a mixture of diethyl ether and pentane (1+1)+1% triethyl amine as eluent. The crude products were triturated in pentane yielding (1R, 2S, 3S)-2-carbomethoxy-3-(4-fluorophenyl)tropane, white crystals m.p. 91–92° C. and (1R, 2R, 3S)-2-carbomethoxy-3-(4-fluorophenyl)tropane, white crystals m.p. 65–66° C.

2) The reaction mixture was cooled to −78° C. and a solution of trifluoroacetic acid (20 ml, 250 mmol) in 50 ml diethyl ether was added over 10 minutes. The cooling bath was removed and when the temperature had reached 0° C. the mixture was stirred into 700 ml water. The pH of the water phase was adjusted to pH 1 by addition of concentrated hydrochloric acid followed by aqueous work up and purification in the same way as described above. This method yielded a mixture of two stereoisomers (2S/2R - 2/1).

The following compounds were made in a similar way:

(1R, 2R, 3S)-2-Carbomethoxy-3-benzyltropane and (1R, 2S, 3S)-2-carbomethoxy-3-benzyltropane, method 2, only (1R, 2S, 3S)-2-carbomethoxy-3-benzyltropane was obtained without contamination of the other isomer, as oil, which crystallize upon standing, m.p. 53–54° C. (1R, 2R, 3S)-2-Carbomethoxy-3-benzyltropane was obtained by isomerisation of the mixture as described in example 3.

(1R, 2R, 3S)-2-Carbomethoxy-3-(4-chlorophenyl)tropane and (1R, 2S, 3S)-2-carbomethoxy-3-(4chlorophenyl)tropane, method 2. The two isomers were not separated but the mixture was isomerized as described in example 3.

(1R, 2R, 3S)-2-Carbomethoxy-3-(4-chlorophenyl)tropane, (1 R, 2S, 3S)-2-carbo-methoxy-3-(4-chlorophenyl)tropane, (1S, 2S, 3R)-2-carbomethoxy-3-(4-chlorophenyl)tropane and (1S, 2R, 3R)-2-carbomethoxy-3-(4-chlorophenyl)tropane, method 2. The two sets of enantiomeric pairs were not separated but the mixture was isomerized as described in example 3.

(1R, 2R, 3S)-2Carbomethoxy-3-(4-methylphenyl)tropane and (1R, 2S, 3S)-2carbomethoxy-3-(4-methylphenyl)tropane, method 2. The two isomers were not separated but the mixture was isomerized as described in example 3.

(1R, 2S, 3S)-2-Carbomethoxy-3-(2-naphthyl)tropane and (1 R, 2R, 3S)-2-carbo-methoxy-3-(2-naphthyl)tropane, method 2. Grignard reagent made by addition of a mixture of one equivalent 2-bromonaphthalene and 1,2-dibromoethane in diethyl ether to a refluxing suspension of two equivalents of magnesium. Both products were white crystalline compounds with m.p. 79–80° C. and 86–87° C. respectively.

(1R, 2R, 3S)-2-Carbomethoxy-3-(1 -naphthyl)tropane and (1R, 2S, 3S)-2-carbo-methoxy-3-(1-naphthyl)tropane, hydrochloride, method 2. Grignard reagent made by addition of a mixture of one equivalent 1 -bromonaphthalene and 1,2-dibromoethane in diethyl ether to a refluxing suspension of two equivalents of magnesium. The title compounds were isolated as respectively a white crystalline compound, m.p.133–135° C. and an amorphous compound.

(1R, 2S, 3S)-2-Carbomethoxy-3-(3,4-dichlorophenyl)tropane and (1R, 2R, 3S)-2-carbomethoxy-3-(3,4-dichlorophenyl)tropane, method 2. Both products were white crystalline compounds with m.p. 69–70° C. and 61–63° C. respectively.

A racemic mixture of (1R, 2R, 3S)-2-Carbomethoxy-3-(3,4-dichlorophenyl)tropane and its enantiomere (1S, 2S, 3R)-2-Carbomethoxy-3-(3,4-dichlorophenyl)tropane, was prepared using (+−)-anhydroecgonine methyl ester as starting material, method 2. followed by isomerisation as described in example 3.

(1S, 2S, 3R)-2-carbomethoxy-3-(3,4-dichlorophenyl)tropane, was prepared using method 2. The compound was not isolated but isomerised as described in example 3.

(1R, 2S, 3S)-2-Carbomethoxy-3-(4-phenyl-phenyl)tropane and (1R, 2R, 3S)-2-carbomethoxy-3-(4-phenyl-phenyl)tropane, method 2. Both products were white crystalline compounds with m.p. 130–132° C. and 95–96° C. respectively. (1R, 2S, 3S)-2-Carbomethoxy-3-(4-t-butyl-phenyl)tropane and (1R, 2R, 3S)-2-carbomethoxy-3-(4-t butyl-phenyl)tropane, method 2. Both products were white crystalline compounds with m.p. 84–85° C. and 83–84° C. respectively.

EXAMPLE 3

(1R, 2R, 3S)-2-Carbomethoxy-3benzyltropane, hydrochloride.

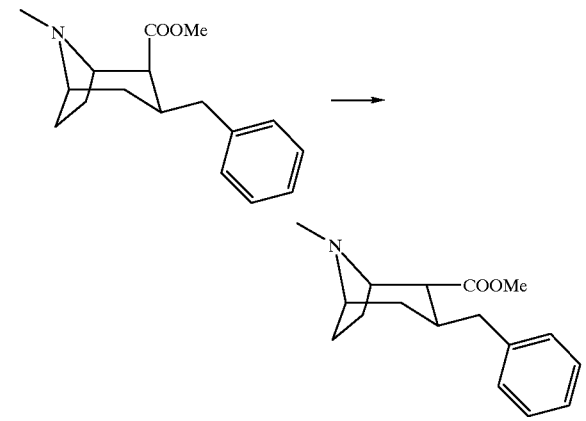

To a solution of (1R, 2S, 3S)-2-carbomethoxy-3-benzyltropane (5.6 g, 20.5 mmol) in absolute methanol (100 ml) was added a solution of sodium methanolate in methanol (2M, 2 ml) and the mixture was refluxed for 16 hours. The reaction mixture was concentrated in vacuo and the residue was dissolved in diethyl ether and was washed with water. The organic phase was dried and concentrated in vacuo. The crude product was purified by column chromatography using a mixture of diethyl ether and pentane (1+1)+1% triethyl amine as eluent yielding (1R, 2R, 3S)-2-carbomethoxy-3-benzyltropane as oil. By dissolution of this product in diethyl ether and subsequent addition of a solution of hydrochloric acid in diethyl ether the title compound precipitated as white crystals, m.p. 188–190° C.

EXAMPLE 4

2-Carbomethoxy-3-tropanone.

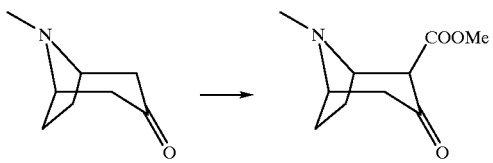

To a suspension of sodium hydride (3.2 g 80%, 107 mmol, prewashed in cyclohexane) and dimethylcarbonate (9.13 ml, 108 mmol) in absolute cyclohexane heated to reflux temperature, a solution of (+−)-3-tropanone (6.9 g, 50 mmol) in 50 ml absolute cyclohexane was added over 15 minutes. No hydrogen evolution was apparent so 0.2 ml methanol was added. The reaction mixture was stirred over night at reflux temperature and after cooling to ambient temperature 75 ml water was carefully added. To the water phase was added 40 g ammonium chloride and the resulting mixture was extracted 8 times with methylene chloride. The combined methylene chloride organic phases were dried and concentrated in vacuo followed by column chromatography of the crude product using methylene chloride with increasing amounts (up to 10%) of methanol as eluent. The fractions containing the product were concentrated in vacuo and the resulting oil was subjected to Kugelrohr destillation (1 mbar, 120° C., yielding the title compound as orange crystals, m.p. 104–107° C.

EXAMPLE 5

2-Carbomethoxy-3-hydroxy-tropane, hydrochloride.

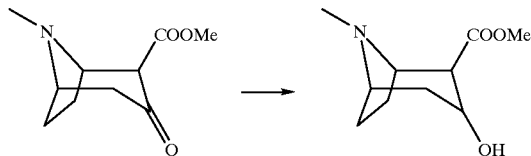

To a solution of the 2-carbomethoxy-3-tropanone obtained in example 4 (17 g, 85 mmol) in 750 ml methanol cooled to −35° C. was added sodium borohydride (17 g, 450 mmol) and the mixture was stirred for 4 hours. The cooled solution was quenched by slow addition of concentrated hydrochloric acid (40 ml) and the mixture was concentrated in vacuo. Water (400 ml) was added and the pH was adjusted to 3 by addition of concentrated hydrochloric acid. After having washed the water phase three times with diethyl ether pH was adjusted to 11 by addition of concentrated ammonium hydroxide and the water phase was extracted three times with methylene chloride. Concentration in vacuo yielded oil which was dissolved in ethanol and added concentrated hydrochloric acid followed by concentration in vacuo. Freeze drying of the residue yielded the title compound as an amorphous product.

(1S)-carbomethoxy-3-hydroxy-tropane, amorphous solid, was made in a similar way using as starting material (1S)-2-carbomethoxy-3-tropanone obtained by resolution as described in *J. Med. Chem.*, 37, 2007(1994),of the compound obtained in example 4.

EXAMPLE 6

(1RS)-Anhydroecgonine methyl ester.

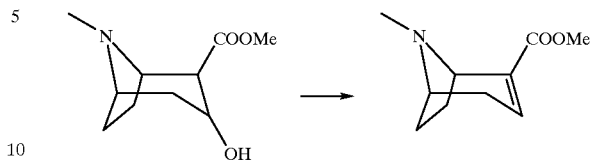

A mixture of 2-carbomethoxy-3-hydroxy-tropane, hydrochloride obtained in example 5 (0.5 g, 2.1 mmol) and thionyl chloride (0.4 ml, 5.3 mmol) was stirred at 60° C. for two hours resulting in a clear solution. After cooling to ambient temperature crushed ice was added and pH was adjusted to 11 by addition of concentrated ammonium hydroxide. The mixture was extracted twice with methylene chloride and the solvent was removed in vacuo yielding the title compound as oil which was destilled, 1 mbar 70–85° C.

(1S)-Anhydroecgonine methyl ester, oil, was made in a similar way using (1S)-carbomethoxy-3-hydroxy-tropane obtained in example 5 as starting material.

EXAMPLE 7

(1R, 2R, 3S)-N-Normethyl-2-carbomethoxy-3-(3, 4dichlorophenyl)tropane

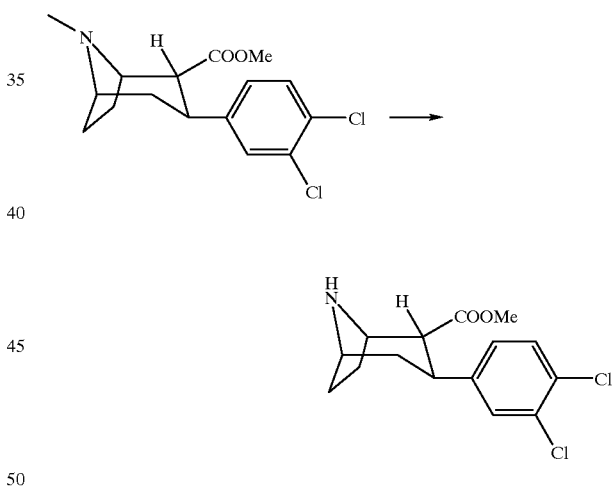

A mixture of (1R, 2R, 3S)-2-carbomethoxy-3-(3,4-dichlorophenyl)-tropane (8.7 g, 27 mmol) and 2, 2, 2-trichloroethyl chloroformate (14.6 ml, 106 mmol) in dry toluen (100 ml) was refluxed for 18 hours. The reaction mixture was concentrated in vacuo and to the residue was added methylene chloride which subsequently was washed with water. The organic phase was dried and concentrated in vacuo. The residue was dissolved in 75% aqueous acetic acid (60 ml) and zinc dust (8.7 g) was added to the reaction mixture which thereafter was stirred at ambient temperature for 18 hours. Concentrated ammonium hydroxide was added (pH>7), and the mixture was extracted twice with diethyl ether. The combined organic phase was dried and concentrated in vacuo yielding the title compound as oil which was used without further purification.

EXAMPLE 8

(1R, 2R, 3S)-N-Normethyl-N-(tert-butoxycarbonyl)-2-carbomethoxy-3-(3,4-dichlorophenyl)tropane

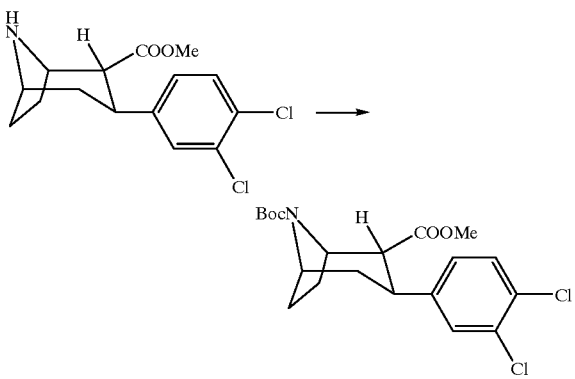

A solution of (1R, 2R, 3S)-N-normethyl-2-carbomethoxy-3-(3,4-dichloro-phenyl)tropane (7 g, 22.3 mmol) and di-tert-butyl-dicarbonate (7.7 ml, 33.6 mmol) in dry tetrahydrofurane (50 ml) was stirred at room temperature for one hour. The reaction was quenched by addition of ice (100 ml) and the mixture was extracted twice with diethylether which was dried and concentrated in vacuo yielding the title compound as oil, which was used without further purification.

EXAMPLE 9

(1R, 2S, 3S)-2-Hydroxymethyl-3-(4-fluorophenyl)tropane.

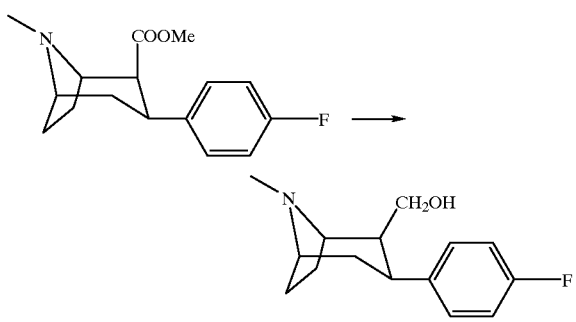

To a suspension of lithium aluminum hydride (0.8 g, 21 mmol) in diethyl ether (30 ml), at room temperature, was slowly added a solution of (1R, 2S, 3S)-2-carbomethoxy-3-(4-fluorophenyl)tropane (5 g, 18 mmol) in 100 ml diethyl ether. The reaction completed after stirring for 10 minutes and was quenched by addition of 0.8 ml water, 0.8 ml sodium hydroxide (15%) and 2 ml water. The aluminum salts were removed by filtration and the solvent was removed in vacuo leaving oil. The title compound precipitated upon trituration with pentane as white crystals, m.p. 79–80° C.

The following compounds were made in a similar way:
(1R, 2R, 3S)-2-Hydroxymethyl-3-(4-fluorophenyl)tropane, white crystals, m.p. 169–170° C.
(1R, 2R, 3S)-2-Hydroxymethyl-3-(3,4-dichlorophenyl)tropane, white crystals, m.p. 145–150° C.
(1R, 2R, 3S)-N-Normethyl-N-(tert-butoxycarbonyl)-2-hydroxymethyl-3-(3,4-dichlorophenyl)tropane, oil.
(1R, 2S, 3S)-2-Hydroxymethyl-3(3,4dichlorophenyl)tropane, white crystals, m.p. 83–89° C.

A racemic mixture of (1R, 2R, 3S)-2-Hydroxymethyl-3-(3,4-dichlorophenyl)tropane and its enantiomere (1S, 2S, 3R)-2-Hydroxymethyl-3-(3,4-dichlorophenyl)tropane, m.p. 186–187° C.
(1S, 2S, 3R)-2-Hydroxymethyl-3-(3,4-dichlorophenyl)tropane, m.p. 179–184° C.
(1R, 2R, 3S)-2-Hydroxymethyl-3-(4-chlorophenyl)tropane, white crystals, m.p. 200–202° C.

EXAMPLE 10

(1R, 2R, 3S)-2-hydroxymethyl-3-(3,4dichlorophenyl)tropane tosylate.

To a suspension of (1R, 2R, 3S)2-hydroxymethyl-3-(3,4-dichlorophenyl)tropane (15 g, 0.05 mol) in methylene chloride (250 mL), was added triethylamine (8 mL) and tosyl chloride (10.5 g, 0.06 mol). The reaction was stirred overnight at room temperature. The solvent was evaporated off and the residue dissolved in ether. The ether phase was washed with sodium hydroxide (1N) and twice with water. Drying over magnesium sulphate and evaporation of the solvent yields 21.1 g (93%) of the corresponding tosylate.

Alternatively, the tosylate was prepared as follows:
To a cold (5°) suspension of (1R, 2R, 3S)-2-hydroxymethyl-3-(3,4dichlorophenyl)tropane (1.5 g, 5 mmol) in pyrdine (5 ml) was added tosyl chloride (1.15 g, 6 mmol). The reaction was stirred at room temperature for 1 hour. Water (50 ml) was added at temperature<10° C. and the mixture was stirred for 15 min. 4N NaOH (2.5 ml) was added. The product was isolated washed with water and dried. Yield 2.12 g (93%).

Re-crystalliaton from 100 ml heptane gave 1.61 g pure tosylate. M.p. 124–125° C.

EXAMPLE 11

(1R, 2R, 3S)-2-Methoxymethyl-3-(3,4-ichlorophenyl)tropane.

(1R, 2R, 3S)-2-hydroxymethyl-3-(3,4-dichlorophenyl)tropane tosylate (9.2 g, 0.02 mol) was dissolved in anhydrous methanol (100 mL). Sodium methoxide in methanol (15 mL 2N. 30 mmol) was added and the reaction was refluxed for 96 hours. The solvent was evaporated off and the residue dissolved in ether. The ether phase was washed three times with water and dried over magnesium sulphate. Evaporation of the solvent yields 5.98 g (95%) of the title compound. M.p. 73–76° C.

(1R, 2R, 3S)-2-Methoxymethyl-3-(3,4dichlorophenyl)tropane, citrate was prepared a follows:
A solution of (1R, 2R, 3S)-2-Methoxymethyl-3-(3,4-dichlorophenyl)tropane (16 g, 50 mmol) in 96% ethanol (200 ml) was added citric acid (10.5 g, 55 mmol). The mixture was heated to a clear solution. The solution was cooled and the precipitate was filtered off and washed with 2×25 ml ethanol. Yield 21.0 g (83%) M.p. 159–150° C.

(1R, 2R, 3S)-2-Methoxymethyl-3-(3,4-dichlorophenyl)tropane sulphate was prepared as follows:
A solution of (1R, 2R, 3S)-2-Methoxymethyl-3-(3,4-dichlorophenyl)tropane (2.2 g, 7 mmol) in isopropanole (10 ml) was added sulphuric acid in isopropanol (2M, 3.6 ml ). The sulphate crystallises upon cooling and seeding. The crystals was filtered off, washed with cold isopropanol and dried. Yield 1.61 g M.p. 171–172° C.

The following compounds was prepared analogously:
(1R, 2R, 3S)-2-isopropoxymethyl-3-(3,4-dichlorophenyl)-tropane, fumarate. M.p. 154–155° C.

(1R, 2R, 3S)-2-cyclopropylmethyloxymethyl-3-(3,4-dichlorophenyl)-tropane, sulphate. M.p. 66–75° C.

(1R, 2R, 3S)-2-methoxymethyl-3-(4-chlorophenyl)-tropane, citrate. M.p. 165'166° C.

(1R, 2R, 3S)-2-ethoxymethyl-3-(4-chlorophenyl)-tropane, citrate. M.p. 166–167

(1R, 2R, 3S)-N-Normethyl-2-ethoxymethyl-3-(4-chlorophenyl)-tropane, fumarate. M.p. 184–186° C.

(1R, 2R, 3S)-N-Normethyl-2-methoxymethyl-3-(4-chlorophenyl)-tropane, citrate. M.p. 112–114° C.

(1R, 2R, 3S)-2-cyclopropylmethyloxymethyl-3-(4-chlorophenyl)-tropane, citrate. M.p. 155–157° C.

(1R, 2R, 3S)-N-normethyl-2-cyclopropylmethyloxymethyl-3-(4-chlorophenyl)-tropane, fumarate. M.p. 176–178° C.

EXAMPLE 13

(1R, 2R, 3S)-2-ethoxymethyl-3-(3,4-dichlorophenyl) tropane.

(1R, 2R, 3S)-2-hydroxymethyl-3-(3,4-dichlorophenyl) tropane tosylate (2.5 g, 5.5 mmol) was dissolved in anhydrous ethanol (20 ml). Sodium ethoxide in ethanol (2.4 ml, 2.5M, 6 mmol) was added and the reaction mixture was refluxed for 72 hours. The solvent was evaporated off. The residue was stirred with water and ether and extracted three times with ether (3×50 ml) and dried over $MgSO_4$. Evaporation of the solvent yields 1.75 g of the title compound. The product was purified by column chromatography on silica using EtOAc:$Et_3$N (99:1). Yield 1.24 g.

The fumarate salt of the above compound was prepared as follows:

A solution of (1R, 2R, 3S)-2-ethoxymethyl-3-(3,4-dichlorophenyl)tropane (450 mg, 1.38 mmol) in ether was added fumaric acid (160 mg, 1.38 mmol) suspended in MeOH and the mixture was heated until a clear solution was obtained. The solution was evaporated and the residue was triturated in ether, seeded and stirred for overnight. The precipitate was filtered off, washed with ether and dried to yield 370 mg of the fumarate salt. M.p. 134–137° C.

EXAMPLE 14

(1R, 2R, 3S)-2-ethoxymethyl-3-(3,4-dichlorophenyl) tropane (1R, 2R, 3S)-2-hydroxymethyl-3(3,4-dichlorophenyl) tropane (26.9 g, 0.09 mol) in THF (200 ml) was added sodium hydride 60% in oil (4.6 g, 0.12 mol) and ethylsulphate (15.7 ml, 0.12 mol) and heated to 30–40° C. on an oil bath for ½ hour. The reaction mixture was stirred at ambient temperature overnight. The reaction mixture is then heated to 30–40° C. on an oil bath for 1 hour and poured into water (500 ml). The mixture was extracted twice with tert.butylmethylether, the organic phases was washed with water and dried over $MgSO_4$ and evaporated to yield the 32.82 g of the title compound.

(1R, 2R, 3S)-2-ethoxymethyl-3-(3,4-dichlorophenyl) tropane citrate was prepared as follows:

A solution of (1R, 2R, 3S)-2-ethoxymethyl-3-(3,4-dichlorophenyl)tropane in 96% ethanol (275 ml) was added citric acid ( 19.2 g, 0.1 mol). The solution was heated to reflux. The solution was left at ambient temperature for 3 hours leading to crystallisation. The mixture was left on icebath for ½ hour, the crystalline product was filtered off and washed with 96% ethanol (50 ml and 25 ml). The crystalline product was dried. Yield 32.85 mg (70%). M.p. 153–155.5° C.

EXAMPLE 15

(1R, 2R, 3S)-N-normethyl-2-methoxymethyl-3-(3, 4dichlorophenyl)-tropane, citrate.

To a solution of (1R, 2R, 3S)-2methoxymethyl-3-(3,4-dichlorophenyl)tropane (5.98 g, 19 mmol) in dichloroethane (50 mL) was added chloroethyl chloroformate (2.7 mL, 25 mmol). The reaction mixture was refluxed overnight. The solvent was evaporated off and the residue refluxed in methanol for 30 min. The solvent was evaporated off and the residue dissolved in water. The solution was made basic with aqueous ammonia and extracted with ether. The ether phase was washed with water, dried with magnesium sulphate and evaporated to dryness to afford 5.4 g. The residue was purified by column chromatography on silica using $CH_2Cl_2$/MeOH/$NH_3$ (aq) (40:9:1). 2.64 g of purified material was obtained. This material was dissolved in ethanol (20 mL, 96%) and citric acid (1.7 g) in ethanol (20 mL, 96%) was added. Standing at 5° C. afforded 3.82 g (41%) crystalline solid, m.p. 118–120° C.

(1R, 2R, 3S)-N-normethyl-2-ethoxymethyl-3-(3,4-dichlorophenyl)-tropane, citrate.

A solution of (1R, 2R, 3S)-2-ethoxymethyl-3-(3,4-dichlorophenyl)tropane (4.85 g, 14.8 mmol) in dichloroethane (50 ml) was added chloroethyl chloroformate (2.4 ml, 22 mmol). The reaction was refluxed overnight. The solvent was evaporated off and the residue refluxed in methanol (50 ml) for 30 min. The solvent was evaporated off and the residue dissolved in water. The solution was made basic with $NH_4OH$ and extracted with ether. The ether phase was washed with water, dried with $Mg_2SO_4$ and evaporated to afford 4.35 g crude product.

The product was purified by column chromatography on silica (100 g) using a mixture of $CH_2Cl_2$/MeOH/$NH_4OH$ (40:9:1) as the eluent. Yield 2.49 g The fumarate salt was formed by dissolving the product in ethanol and adding fumaric acid in ethanol (0.25M). The salt was filtered off, washed with ethanol and dried. M.p. 220–222° C.

EXAMPLE 16

(1R, 2R, 3S)-2-ethylthiomethyl-3-(3,4-dichlorophenyl) tropane

To a cold (0° C.) solution of ethanethiol (0.5 ml) in dimethylformamide (30 mL) was added sodium hydride (60%, 0.27 g). When the evolution of hydrogen had ceased (1R, 2R, 3S)-2-tosylmethyl-3-(3,4dichlorophenyl)tropane (2.0 g, 4.4 mmol) in dimethylformamide (20 ml) was added. The mixture was stirred at 0° C. for 25 min. The reaction mixture was heated at 100° C. for 5 days. The reaction was cooled to ambient temperature and poured into a mixture of water (500 ml) and ether (100 ml). The phases were separated and the aqueous phase was extracted once more with ether (100 ml). The ether phase was evaporated and the residue was dissolved in ether (75 ml) and washed with water (2×400 ml), dried over $MgSO_4$ and evaporated to dryness. Yield: 1.4 g. of the tite compound. The crude product was purified by column chromatography on silica gel using a mixture of $CH_2Cl_2$/MeOH $NH_3$ (aq) (9:1) +1% $NH_3$ (aq). 0.6 g of the title compound was obtained as an oil.

To a suspension of (1R, 2R, 3S)-2-ethylthiomethyl-3-(3, 4dichlorophenyl)tropane (0.3 g) in ether (3–4 ml) was added fumaric acid (1.02 eqv.) in warm MeOH (4 ml). The solution was seeded and left at ambient temperature overnight. The crystalline product was isolated by filtration. The crystals were suspended in petroleumether, stirred for 30 min, isolated by filtration and dried. Yield 0.38 g, M.p. 69–71° C.

What is claimed is:

1. A method of treating a mammal suffering from Alzheimer's disease, which method comprises the step of administering to said mammal a therapeutically effective amount of 2,3- trans-di-substituted tropane compound having the formula or any mixture thereof, or a pharmacetically acceptable salt thereof;
wherein
R is hydrogen, methyl, ethyl, or propyl;
$R^3$ is —$CH_2$—X—R', wherein X is O, S, and R' is methyl, ethyl, propyl, or cyclopropylmethyl; and
$R^4$ is phenyl, which may be substituted one or more times with substituents selected from the group consisting of halogen, $CF_3$, and CN.

2. The method of claim 1, wherein in the 2,3-trans-di-substituted tropane compound,
R is hydrogen or methyl;
$R^3$ is —$CH_2$—O—R', wherein R' is methyl, ethyl, isopropyl or cyclopropylmethyl; and
$R^4$ is phenyl, which may be substituted one or more times with halogen.

3. The method of claim 1, wherein in the 2,3-trans-di-substituted tropane compound,
R is hydrogen or methyl;
$R^3$ is —$CH_2$—O—R', wherein R' is methyl, ethyl; and
$R^4$ is 3,4-dichlorophenyl.

4. The method of claim 1 wherein the tropane compound is:
2-methoxymethyl-3-(3,4-dichlorophenyl)-tropane,
2-isopropoxymethyl-3-(3,4-dichlorophenyl)-tropane,
2-ethoxymethyl-3-(3,4-dichlorophenyl)-tropane,
2-cyclopropylmethyloxymethyl-3-(3,4-dichlorophenyl)-tropane,
2-methoxymethyl-3-(4-chlorophenyl)-tropane,
N-Normethyl-2-methoxymethyl-3-(4-chlorophenyl)-tropane,
2-ethoxymethyl-3-(4-chlorophenyl)-tropane,
N-normethyl-2-methoxymethyl-3(3,4-dichlorophenyl)-tropane,
N-normethyl-2-ethoxymethyl-3-(3,4-dichlorophenyl)-tropane,
N-Normethyl-2-ethoxymethyl-3-(4-chlorophenyl)-tropane,
2-ethylthiomethyl-3-(3,4-dichlorophenyl)-tropane,
2-cyclopropylmethyloxymethyl-3-(4-chlorophenyl)-tropane, or
N-normethyl-2-cyclopropylmethyloxymethyl-3-(4-chlorophenyl)-tropane,
or a pharmaceutically acceptable addition salt thereof.

5. A method of claim 1 wherein the tropane compound is:
(1R, 2R, 3S)-2-methoxymethyl-3-(3,4-dichlorophenyl)-tropane,
(1R, 2R, 3S)-2-isopropoxymethyl-3-(3,4-dichlorophenyl)-tropane,
(1R, 2R, 3S)-2-ethoxymethyl-3-(3,4-dichlorophenyl)-tropane,
(1R, 2R, 3S)-2-cyclopropylmethyloxymethyl-3-(3,4-dichlorophenyl)-tropane,
(1R, 2R, 3S)-2-methoxymethyl-3-(4-chlorophenyl)-tropane,
(1R, 2R, 3S)-N-Normethyl-2-methoxymethyl-3-(4-chlorophenyl)-tropane,
(1R, 2R, 3S)-2-ethoxymethyl-3-(4-chlorophenyl)-tropane,
(1R, 2R, 3S)-N-normethyl-2-methoxymethyl-3-(3,4-dichlorophenyl)-tropane,
(1R, 2R, 3S)-N-normethyl-2-ethoxymethyl-3-(3,4-dichlorophenyl)-tropane,
(1R, 2R, 3S)-N-Normethyl-2-ethoxymethyl-3-(3,4-dichlorophenyl)-tropane,
(1R, 2R, 3S)-N-normethyl-2-cyclopropylmethyloxymethyl-3-(4-chlorophenyl)-tropane,
(1R, 2R, 3S)-2-cyclopropylmethyloxymethyl-3-(4-chlorophenyl)-tropane, or
(1R, 2R, 3S)-2-ethylthiomethyl-3-(3,4dichlorophenyl)-tropane,
or a pharmaceutically acceptable addition salt thereof.

6. The method of claim 1 wherein the tropane compound is:
(1R, 2R, 3S)-2-methoxymethyl-3-(3,4-dichlorophenyl)-tropane;
(1R, 2R, 3S)-2-ethoxymethyl-3-(3,4-dichlorophenyl) tropane;
(1R, 2R, 3S)-2-isopropoxymethyl-3-(3,4-dichlorophenyl)-tropane;
(1R, 2R, 3S)-N-normethyl-2-methoxymethyl-3-(3,4-dichlorophenyl)-tropane;
(1R, 2R, 3S)-N-normethyl-2-ethoxymethyl-3-(3,4-dichlorophenyl)-tropane;
or a pharmaceutically acceptable addition salt thereof.

7. The method of claims 1, 2, 3, 4, 5 or 6, wherein the mammal is a human.

* * * * *

UNITED STATES PATENT AND TRADEMARK OFFICE
CERTIFICATE OF CORRECTION

PATENT NO. : 6,395,748 B2
DATED : May 28, 2002
INVENTOR(S) : Scheel-Kruger et al.

It is certified that error appears in the above-identified patent and that said Letters Patent is hereby corrected as shown below:

Column 3,
Line 29, delete "cydoalkyl" and insert -- cycloalkyl --, therefor.
Line 31, delete "mothylenedioxyphenyl" and insert -- methylenedioxypehnyl --, therefor.

Column 4,
Line 5, delete "4dichlorophenyl" and insert -- 4-dichlorophenyl --, therefor.

Column 6,
Line 22, delete "diastereomenic" and insert -- diastereomeric --, therefor.

Column 8,
Line 49, delete "0-40" and insert -- 0-4 --, therefor.
Line 64, delete "issue" and insert -- tissue --, therefor.

Column 20,
Line 48, delete "a" and insert -- as --, therefor.

Column 23,
Line 25, delete "O," and insert -- O or --, therefor.

Column 24,
Line 8, delete "A method" and insert -- The method --, therefor.
Line 52, after "tropane" insert -- or --.

Signed and Sealed this

Fourteenth Day of January, 2003

JAMES E. ROGAN
*Director of the United States Patent and Trademark Office*